United States Patent
Welzig et al.

(10) Patent No.: US 8,372,979 B2
(45) Date of Patent: Feb. 12, 2013

(54) PROCESS FOR THE PRODUCTION OF HIGH-PURITY 2,4'-DIMETHYL-3-PIPERIDINO-PROPIOPHENONE (TOLPERISONE), PHARMACEUTICAL COMPOSITIONS THAT CONTAIN THE LATTER, AS WELL AS ACTIVE INGREDIENT FORMULATIONS THAT CONTAIN TOLPERISONE

(75) Inventors: Stefan Welzig, Vienna (AT); Jan Rothenburger, Oslip (AT); Beate Kälz, Steinbrunn (AT); József Gungl, Sopron (HU); Klaus Gerdes, Vienna (AT); Federico Gaeta, Mountain View, CA (US)

(73) Assignee: SANOCHEMIA Pharmazeutika AG, Vienna (AT)

( * ) Notice: Subject to any disclaimer, the term of this patent is extended or adjusted under 35 U.S.C. 154(b) by 377 days.

(21) Appl. No.: 12/597,722

(22) PCT Filed: Apr. 24, 2008

(86) PCT No.: PCT/AT2008/000149
§ 371 (c)(1),
(2), (4) Date: Mar. 2, 2010

(87) PCT Pub. No.: WO2008/131469
PCT Pub. Date: Nov. 6, 2008

(65) Prior Publication Data
US 2010/0150995 A1 Jun. 17, 2010

Related U.S. Application Data

(60) Provisional application No. 61/027,287, filed on Feb. 8, 2008.

(30) Foreign Application Priority Data

Apr. 26, 2007 (AT) .................................. A 658/2007
Nov. 29, 2007 (AT) ................................ A 1953/2007

(51) Int. Cl.
C07D 295/107 (2006.01)

(52) U.S. Cl. ........................................ 546/236; 546/237
(58) Field of Classification Search .................. 546/236, 546/237
See application file for complete search history.

(56) References Cited

U.S. PATENT DOCUMENTS

| | | | |
|---|---|---|---|
| 4,996,058 | A | 2/1991 | Sinnreich |
| 5,073,375 | A | 12/1991 | Yoshida et al. |
| 5,780,057 | A | 7/1998 | Conte et al. |
| 6,500,455 | B1 | 12/2002 | Frantsits |
| 6,861,072 | B1 | 3/2005 | Alaux et al. |
| 7,385,060 | B2 | 6/2008 | Czollner et al. |
| 2005/0196451 | A1 | 9/2005 | Bodenteich et al. |
| 2006/0004050 | A1 | 1/2006 | Speicher et al. |
| 2006/0041141 | A1 | 2/2006 | Czollner et al. |
| 2006/0198888 | A1 | 9/2006 | Bodenteich et al. |
| 2008/0226713 | A1 | 9/2008 | Bodenteich et al. |
| 2009/0253743 | A1 | 10/2009 | Gaeta et al. |
| 2009/0298893 | A1 | 12/2009 | Alken et al. |
| 2010/0249423 | A1 | 9/2010 | Welzig et al. |
| 2010/0324090 | A1 | 12/2010 | Gaeta et al. |

FOREIGN PATENT DOCUMENTS

| | | |
|---|---|---|
| AT | 500144 A1 | 11/2005 |
| AT | 413539 B | 3/2006 |
| AT | 505225 | 11/2008 |
| EP | 0717988 A1 | 6/1996 |
| GB | 2163648 A | 3/1986 |
| JP | 53-40779 | 4/1978 |
| JP | 54-27571 | 3/1979 |
| JP | 54-30178 | 3/1979 |
| JP | 54-32480 | 3/1979 |
| JP | 54-36274 | 3/1979 |
| JP | 4-5283 A | 1/1992 |
| WO | 2004/032927 A1 | 4/2004 |
| WO | 2004/050648 | 6/2004 |
| WO | 2005/084676 | 9/2005 |
| WO | WO 2005/094825 A1 | 10/2005 |
| WO | WO 2008/133937 A2 | 11/2008 |
| WO | WO 2009/013552 A1 | 1/2009 |

OTHER PUBLICATIONS

Braga et al. "Making crystals . . . " Royal Soc, Chem. Chem. Commun. p. 363503645 (2005).*
Cheronis "Seminicro expe . . . " p. 31-43 (1958).*
Davies "Changing the salt changing the drug" Phar, J. v.266(7138) p. 322-323 (2001).*
Kirk-Othmer "Crystallization" Encyclopedia of Chem. tech. p. 95-147 (2002).*
Seddon "Pseudomorph . . . " Crystal growth and design 4(6) 1087 (2004)(2 page from internet.*

(Continued)

Primary Examiner — Celia Chang
(74) Attorney, Agent, or Firm — Cooley LLP

(57) ABSTRACT

The invention relates to a method for producing highly pure 2,4'-dimethyl-3-piperidino-propiophenone (tolperisone) (formula I) and the pharmaceutically acceptable salts, hydrochlorides, and hydrates thereof. The method allows the content of the undesired byproduct 2-methyl-1-(4-methylphenyl) propenone (4-MMPPO) to be kept significantly lower than in previously known methods. The invention further relates to active substance formulations which contain tolperisone and are suitable, among other things, for producing combination preparations used for treating patients suffering from Alzheimer's disease. The invention also relates to topical formulations, controlled release (CR) formulations, and transdermal therapeutic systems, such as active substance patches, which contain less than 50 ppm, preferably less than 10 ppm, more preferably less than 7 ppm, and most preferably less than 3 ppm or 0 ppm (i.e. less than the detectable amount) of the undesired byproduct 2-methyl-1-(4-methylphenyl) propenone (4-MMPPO) in relation to 100 percent by weight of active substance.

27 Claims, No Drawings

OTHER PUBLICATIONS

Sumita et al. "A modified Mannich . . . " CASREACT 122:264610 (1994).*
Sumita et al. "A modified Mannich . . . " Chem. Pharm. Bull. 42(8) 1676-1678 (1994).*
Tolperisone "ChemBook-structure" p. 1 (2012).*
Tolperisone HCI "ChemBook structure" p. 1 (2012).*
Vippagunta et al. Crystalline solids: Adv. Drug. Delivery Rev. 48 p. 3-26 (2001).*
International Search Report dated Mar. 11, 2009, from corresponding PCT application.
Search Report in corresponding A 195/2007 dated Feb. 20, 2008.
Search Report in corresponding A658/2007 dated Feb. 19, 2008.
Dietrich and Fels, "Synthesis of $^3$H-Tolperisone," J. Label. Compounds Radiopharm. 42:1125-1134 (1999).
European Search Report for Appl. No. EP 10450026, 7 pages (Jul. 5, 2011).
International Search Report and Written Opinion for PCT appl. No. PCT/US2008/005281, 12 pages (Nov. 5, 2008).
Ono et al., "Mechanisms of Depressant Action of Muscle Relaxants on Spinal Reflexes: Participation of Membrane Stabilizing Action," J. Pharm. Dyn. 7(3):171-176 (1984).
Sae-Lee and Sae-Lee, "The Effect of Temperature on Stability of Tolperisone Hydrochloride Solution," Thai Pharm. Health Sci. J. 11(1):1-4 (2006).
Velmurugan et al., "Optimization of the Reversed-Phase High-Performance Liquid Chromatographic Separation of the Enantiomers of a Cationic Chiral Drug (Tolperisone) on a Heptakis(6-Azido-6-deoxy) Perphenylcarbamated β-Cyclodextrin Column," Chromatographia 56(3-4):229-232 (2002).

* cited by examiner

PROCESS FOR THE PRODUCTION OF HIGH-PURITY 2,4'-DIMETHYL-3-PIPERIDINO-PROPIOPHENONE (TOLPERISONE), PHARMACEUTICAL COMPOSITIONS THAT CONTAIN THE LATTER, AS WELL AS ACTIVE INGREDIENT FORMULATIONS THAT CONTAIN TOLPERISONE

The invention relates to a process for the production of high-purity 2,4'-dimethyl-3-piperidino-propiophenone (tolperisone), its pharmaceutically acceptable salts, hydrochlorides and hydrates, pharmaceutical compositions that contain the latter, as well as tolperisone-containing active ingredient formulations, tolperisone-containing topical formulations, tolperisone-containing controlled release (CR) formulations, and tolperisone-containing, transdermal, therapeutic systems, such as active ingredient patches.

Tolperisone is a muscle-relaxing agent (muscle relaxant) with the formula below

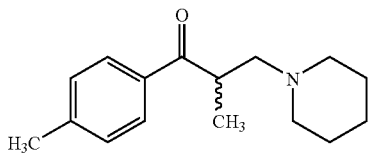 [SMILES: Cc1ccc(C(=O)C(C)CN2CCCCC2)cc1]

Main indications of tolperisone are diseases that are accompanied by painful muscle cramps, e.g., spinal column syndrome, muscular pain in degenerative diseases, work-related and sports-related stress syndrome and the fibromyalgia syndrome.

One advantage of the treatment with tolperisone is that even functional parameters, such as, e.g., the mobility of the patient, are improved. Because of the absence of central side effects, patients with long-term intake of tolperisone generally have a good therapeutic ratio and the basis for confidence necessary for success of the therapy in further use of this medication. One requirement in this respect is that the active ingredient tolperisone is produced in the purest possible form and thus the proportion of undesired by-products is kept as low as possible.

Processes for the production of tolperisone are known from: AT 413 539, U.S. Patent Application Publication No. 20060041141; Ditriech et al. (1999) J. Labeled Cpd. Radiopharm 42: 1125-1134; Jap. Pat. 04005283 19920109; Jap. Pat. 54032480 19790309; Jap. Pat. 54036274 19790316; Jap. Pat. 54030178 19790306; Jap. Pat. 54027571 19790301; Kazuharu et al. (1994) Chem. Pharm. Bulletin 42 (8) 1676; Jap. Pat. 20, 390 (1965); and Hung. Pat. 144,997 (1956).

None of the latter, however, describes any method that makes possible a process for permanent removal and stabilization of the especially critical contamination of 2-methyl-1-(4-methylphenyl)-propenones (4-MMPPO), nor is a process described for removal of the contamination of 2-methyl-1-(4-methyl-phenyl)-propenones (4-MMPPO) in the ppm range.

The basic drawback of this synthesis method is that the tolperisone-containing end product that is obtained contains undesired substances, in particular 4-MMPPO, in such concentrations because of secondary reactions and chemical contaminants, and can form under storage conditions, which are toxic for tolperisone-treated patients.

Based on the synthesis methods that are used, the following contaminants in the active ingredient tolperisone are found: piperidine hydrochloride, 2-methyl-1-(3-methylphenyl)-3-(1-piperidinyl)-propanone hydrochloride (3-tolperisone hydrochloride), 1-(4-methylphenyl)-propanone (4-methyl-propiophenone), 2-methyl-1-(4-methylphenyl)-propenone (4-MMPPO), as well as 2-methyl-1-(2-methylphenyl)-3-(1-piperidinyl)-propanone hydrochloride (2-tolperisone hydrochloride).

An overview with respect to possible contaminations can be seen in the following table:

| Designation | Chemical Name | Chemical Structure |
|---|---|---|
| Piperidine HCl | Piperidine Hydrochloride | 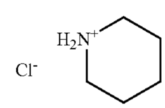 |
| C | 2-Methyl-1-(3-methylphenyl)-3-(1-piperidinyl)-propanone-hydrochloride or 3-Tolperisone Hydrochloride | 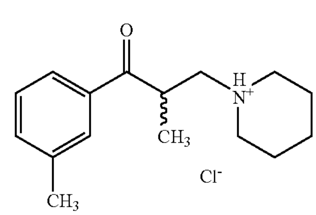 |
| 4-MPP | 1-(4-Methylphenyl)-propanone or 4-Methylpropiophenone | 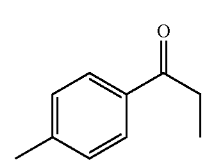 |

-continued

| Designation | Chemical Name | Chemical Structure |
|---|---|---|
| 4-MMPPO | 2-Methyl-1-(4-methylphenyl)-propenone | 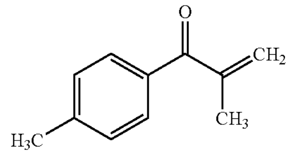 |
| D | 2-Methyl-1-(2-methylphenyl)-3-(1-piperidinyl)-propanone Hydrochloride or 2-Tolperisone Hydrochloride | 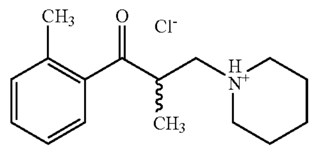 |

Special attention must be paid regarding the contamination of 2-methyl-1-(4-methylphenyl)-propenone (4-MMPPO), since the latter has to be classified as potentially genotoxic because of its chemical structure and preclinical in vitro tests. The latest guidelines of the FDA and EMEA relative to genotoxic substances (Guideline on the Limits of Genotoxic Impurities CPMP/SWP/5199/02) define the maximum contents of these substances at <1.5 μg/day in pharmaceutical active ingredients, which, at the dosages of tolperisone that are common in treatment, leads to a potential boundary value of between at most 25 and 1 ppm of 4-MMPPO in the active ingredient and in the finished product. Approval of the FDA for a tolperisone formulation is then possible only if the values do not drop below these boundary values.

Independently of the respective, previously known synthesis, the known, undesired by-product 2-methyl-1-(4-methylphenyl)-propenone (4-MMPPO) with the following formula:

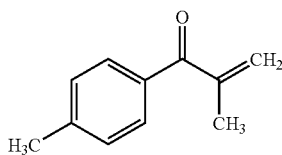

is always produced.

The by-product 4-MMPPO is formed from tolperisone by beta-elimination:

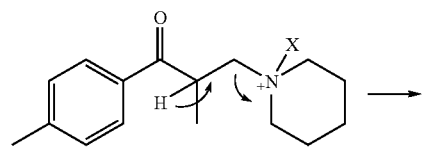

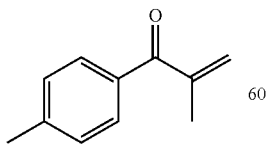

This undesired secondary reaction is carried out both in the production of tolperisone and in its storage. This applies both for the active ingredient and for pharmaceutical formulations, in whose production and storage 4-MMPPO can also be produced as a degradation product. The following table provides an overview on 4-MMPPO concentrations in commercial tolperisone formulations:

| Sample | Product | Lot | Production Date | 4-MMPPO in ppm |
|---|---|---|---|---|
| 1 | Mydeton | T666T2A | July 2006 | 215 |
| 2 | Mydeton | T6A207A | October 2006 | 107 |
| 3 | Mydocalm | 506223 | May 2005 | 442 |

One object of this invention is therefore to propose a process for the production of high-purity 2,4'-dimethyl-3-piperidino-propiophenone (tolperisone), its pharmaceutically acceptable salts, hydrochlorides and hydrates, with which the proportion of 2-methyl-1-(4-methylphenyl)-propenone (4-MMPPO) is achieved in any case under the maximum values required by the FDA and EMEA.

According to the invention, a process of the above-mentioned type is proposed, in which 4-methylpropiophenone

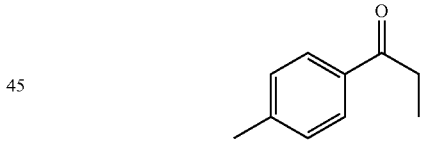

is reacted with piperidine hydrochloride

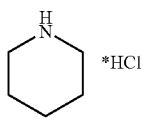

and 1,2-dioxolan

in the presence of one or more acids as a catalyst, and tolperisone is filtered off from the reaction mixture as a crude product in free form or in the form of its pharmaceutically compatible hydrochlorides, hydrates and additional salts after cooling, and whereby by recrystallization of the tolperisone crude product, the proportion of 2-methyl-1-(4-methylphenyl)-propenone (4-MMPPO) is reduced. With the process according to the invention, the proportion of 4-MMPPO can be considerably reduced and in particular can be scaled down to "zero," so that the tolperisone that can be obtained according to the invention contains no 4-MMPPO or 4-MMPPO in portions just below the detection limit.

For example, the proportion of tolperisone in 4-MMPPO that can be obtained according to the invention can be reduced to less than 0.15% by weight relative to 100% by weight of crude product.

The process according to the invention also allows that the proportion of 2-methyl-1-(4-methylphenyl)-propenone (4-MMPPO) is reduced to less than 0.15% by weight, in particular to less than 0.002% by weight relative to 100% by weight of tolperisone crude product. In this case, it is possible that the proportion of 2-methyl-1-(4-methylphenyl)-propenone (4-MMPPO) is reduced to less than 10 ppm. In particular, the proportion of 2-methyl-1-(4-methylphenyl)-propenone (4-MMPPO) can be reduced to less than 7 ppm or to less than 3 ppm. Finally, the process according to the invention allows that the proportion of 2-methyl-1-(4-methylphenyl)-propenone (4-MMPPO) is reduced to less than 1.5 ppm or to 0 ppm (i.e., below the detection limit).

Advantageous configurations of this process are disclosed according to subclaims.

In addition, the process according to the invention makes it possible to lower the proportion of the contamination of piperidine hydrochloride, which is used both as a crude substance and a degradation product that is produced together with 4-MMPPO, to values of below 100 ppm to 0 ppm (detection limit).

The invention also relates to pharmaceutical formulations that contain the active ingredient tolperisone that is produced according to the process according to the invention in free form or in the form of its pharmaceutically acceptable salts, hydrochlorides and hydrates in connection with one or more pharmaceutically compatible vehicle(s). Possible forms of administration are tablets, capsules, granules, suspensions, syrups, gels, ointments and creams, as well as transdermally therapeutic systems, such as active ingredient patches.

According to the invention, tolperisone is used as an active ingredient in pure form, in the form of its salts, hydrochlorides or hydrates, as well as 2-methyl-1-(4-methylphenyl)-propenone (4-MMPPO) in a proportion of less than 50 ppm, preferably less than 10 ppm, especially preferably less than 7 ppm, and extremely preferably less than 3 ppm or 0 ppm (i.e., below the detection limit) relative to 100% by weight of active ingredient.

As tablets, preferably film tablets with instant-release properties are proposed, in which the active ingredient tolperisone, its salts, hydrochlorides and hydrates are present in connection with a pharmaceutical vehicle and at least one additive, namely a pharmaceutically compatible acid, preferably anhydrous citric acid. For the production of these film tablets, the procedure is performed under anhydrous conditions using solvents.

An especially advantageous pharmaceutical formulation is then prepared if the active ingredient tolperisone is present in embedded form in a matrix, so that a specific release of active ingredient (controlled release) is achieved.

Another especially advantageous pharmaceutical formulation is then made ready if the formulation that contains the active ingredient tolperisone, produced according to the process according to the invention, its salts, hydrochlorides and hydrates is produced on the basis of a mixture that consists of carbomer, sodium hydroxide solution, an alcohol and water with the addition of a stabilizing, pharmaceutically compatible acid, preferably citric acid, with the formation of a gel.

Another especially advantageous pharmaceutical formulation is then made ready if the formulation that contains the active ingredient tolperisone, produced according to the process according to the invention, its salts, hydrochlorides and hydrates is produced on the basis of a mixture that consists of cetyl stearyl alcohol, wool wax alcohols, and Vaseline with the addition of a stabilizing, pharmaceutically compatible acid, preferably citric acid, with the formation of an ointment.

Another especially advantageous pharmaceutical formulation is then made ready if the formulation that contains the active ingredient tolperisone, produced according to the process according to the invention, its salts, hydrochlorides and hydrates is produced on the basis of a mixture that consists of polysorbate, cetyl stearyl alcohol, glycerol, Vaseline, wool wax alcohols, and water with the addition of a stabilizing pharmaceutically compatible acid, preferably citric acid, with the formation of a cream.

Since tolperisone is used as a muscle relaxant in chronic diseases such as multiple sclerosis (MS), there is a need for forms of administration that ensure a slow, steady release of the active ingredient. A TTS, a transdermal therapeutic system, is the suitable form of administration here.

The TTS consists of an active ingredient-impermeable back side, for example a polymer film or a metal foil, preferably made of aluminum. The reservoir layer that is attached to the back side consists of a polymer matrix and the active ingredient embedded therein. According to the invention, tolperisone is used as an active ingredient in pure form, in the form of its salts, hydrochlorides or hydrates, as well as 2-methyl-1-(4-methylphenyl)-propenone (4-MMPPO) in a proportion of less than 50 ppm, preferably less than 10 ppm, especially preferably less than 7 ppm, and extremely preferably of less than 3 ppm or 0 ppm (i.e., below the detection limit) relative to 100% by weight of active ingredient.

In this case, the polymer matrix consists of a base polymer and common additives. Exemplary polymers are rubber, synthetic homo-, block- and co-polymers, polyacrylates, polyurethanes and silicones.

Softeners, such as higher alcohols, glycerides, as well as polyethoxylated alcohols are added to the base polymer.

As penetration aids, physiologically harmless carboxylic acids are used.

The transdermal, therapeutic system according to the invention is produced by the active ingredient together with the components of the contact-adhesive reservoir layer optionally being mixed homogeneously in solution and being applied to the active ingredient-impermeable back side, whereupon optionally the solvent or solvents are removed. Then, the adhesive layer is provided with a corresponding protective layer.

The invention also relates to a process for the production of pharmaceutical formulations that contain the active ingredient tolperisone, produced according to the process according to the invention, its salts, hydrochlorides and hydrates, whereby the active ingredient is mixed under anhydrous conditions in one or more solvent(s) with at least one anhydrous additive, namely a pharmaceutically compatible acid, preferably citric acid, applied on the pharmaceutical vehicle, and converted into the form of administration that is desired in each case. The use of acid as well as working under anhydrous conditions ensure a removal of the 4-MMPPO content during the formulation production as well as also a stabilization of the product during the storage.

The invention also relates to an active ingredient formulation that contains tolperisone in pure form, in the form of its salts, hydrochlorides or hydrates as well as 2-methyl-1-(4-methylphenyl)-propenone (4-MMPPO) in a proportion of less than 50 ppm, preferably less than 10 ppm, especially preferably less than 7 ppm, and extremely preferably less than 3 ppm or 0 ppm (i.e., below the detection limit) relative to 100% by weight of the active ingredient formulation.

The addition of an acidic stabilizer is especially advantageous, since in the storage of the active ingredient formulation, there is the risk that in the presence of a base, 2-methyl-1-(4-methylphenyl)-propene (4-MMPPO) is formed according to the following reaction diagram:

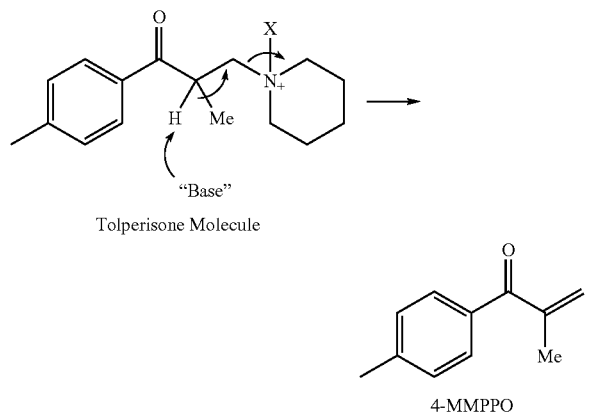

Tolperisone Molecule

4-MMPPO

If an acidic stabilizer, such as an inorganic or organic acid that is compatible to the human body is added as a stabilizer to the active ingredient formulation, this undesired secondary reaction can be prevented:

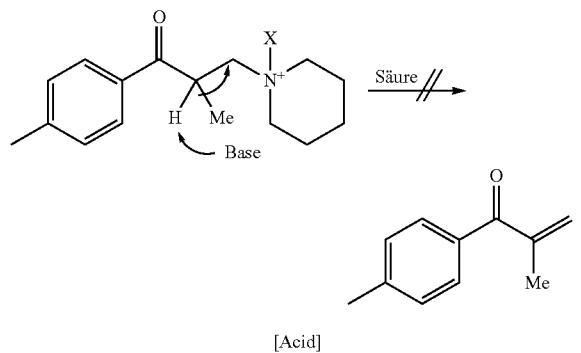

[Acid]

The invention also relates to the use of the active ingredient formulation according to the invention for the production of pharmaceutical agents for treatment and therapy of neurodegenerative diseases, such as Alzheimer's disease.

Surprisingly enough, in the therapy of patients who are suffering from Alzheimer's disease, it was found that the tolperisone-containing active ingredient formulation according to the invention in combination with known preparations for treating Alzheimer's disease considerably improves the physical and mental state of the patients. In the therapy of an 84-year-old patient, who could no longer speak because of advanced disease, memantine was administered in combination with the tolperisone-containing active ingredient formulation according to the invention. After about two weeks, the patient began to speak and also identified the nursing staff, which unquestionably can be attributed to the combination therapy that is applied and that also can take place with other known preparations for treatment of Alzheimer's disease, such as acetyl cholinesterase inhibitors.

The invention also relates to topical formulations that as active ingredient contain tolperisone in pure form, in the form of its salts, hydrochlorides or hydrates as well as 2-methyl-1-(4-methylphenyl)-propenone (4-MMPPO) in a proportion of less than 50 ppm, preferably less than 10 ppm, especially preferably less than 7 ppm, and extremely preferably less than 3 ppm or 0 ppm (i.e., below the detection limit) relative to 100% by weight of active ingredient as well as the additives that are common for topical formulations.

The invention also relates to a controlled release (CR) formulation that contains a core and at least one retard coating that is applied to the core, whereby the core contains components in which the active ingredient tolperisone is embedded in pure form, in the form of its salts, hydrochlorides or hydrates as well as 2-methyl-1-(4-methylphenyl)-propenone (4-MMPPO) in a proportion of less than 50 ppm, preferably less than 10 ppm, especially preferably less than 7 ppm, and extremely preferably less than 3 ppm or 0 ppm (i.e., below the detection limit), relative to 100% by weight of active ingredient.

The invention also relates to a transdermal, therapeutic system, such as an active ingredient patch, comprising a reservoir layer, in which the active ingredient tolperisone is embedded in pure form, in the form of its salts, hydrochlorides or hydrates, as well as 2-methyl-1-(4-methylphenyl)-propenone (4-MMPPO) in a proportion of less than 50 ppm, preferably less than 10 ppm, especially preferably less than 7 ppm, and extremely preferably less than 3 ppm or 0 ppm (i.e., below the detection limit) relative to 100% by weight of active ingredient.

The invention is explained below based on possible embodiments for implementing the invention.

Examples of possible embodiments of the invention and a comparison to the prior art according to AT 413 539 can be seen from the following table:

| Variant | Recrystallization Conditions | Washing Conditions | Drying | 4-MMPPO in ppm |
|---|---|---|---|---|
| Prior Art | Heating in MEK/IPA | Washing with MEK | 45-85° C. | =500 ppm |
| I | Heating of MEK/IPA + Adsorption Agent + 2$^{nd}$ Recrystallization | Washing with MEK | 45-85° C. | =130 ppm |
| II | Heating in MEK/IPA | Washing with IPA with 1% HCl | 45-85° C. | ≦10 ppm, i.e., 1.5 to 10 ppm |
| III | Heating in MEK/IPA + 1% HCl | Washing with MEK | 45-85° C. | ≦10 ppm, i.e., 0 (Not Detectable) to 10 ppm |
| IIIa | Heating in MEK/IPA + 1% HCl + 5% Citric Acid | Washing with MEK | 45-85° C. | ≦10 ppm, i.e., 0 (Not Detectable) to 10 ppm |
| IV | Heating in MEK/IPA + 1% HCl + 5% Citric Acid | Washing with MEK + 1% HCl + 5% Citric Acid | 45-85° C. | 0 (Not Detectable) to 8 ppm |

-continued

| Variant | Recrystallization Conditions | Washing Conditions | Drying | 4-MMPPO in ppm |
|---|---|---|---|---|
| V | Heating in MEK/IPA + 1% HCl + 5% Citric Acid | 1. Washing with MEK + 1% HCl + 5% Citric Acid 2. Washing with MtBE | 50° C. | 0 (Not Detectable) to 5 ppm |
| Va | Heating in MEK/IPA + 1% HCl + 5% Citric Acid | 1. Washing with MEK + 1% HCl 2. Washing with MtBE + 5% Citric Acid | 50° C. | 0 (Not Detectable) to 1 ppm |

The tolperisone crude product is produced according to the following synthesis diagram:

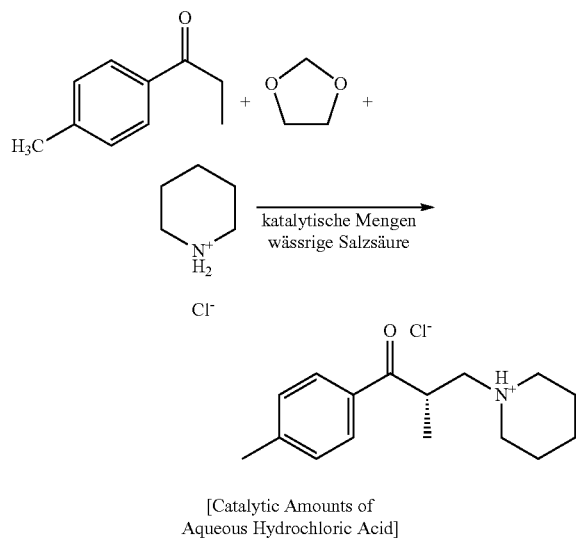

[Catalytic Amounts of Aqueous Hydrochloric Acid]

As a starting material, 4-methylpropiophenone, piperidine hydrochloride and 1,2-dioxolan are used as reactants and also as solvents. The use of 1,2-dioxolan instead of formaldehyde and the high yield after the direct isolation of the tolperisone crude product make the one-stage reaction economical even on an industrial scale.

The purification of the tolperisone crude product by recrystallization is explained in more detail based on the following possible variants as well as a comparison example according to the prior art:

Prior art according to AT PS 413 539: The tolperisone crude product is dissolved under reflux for 30 minutes in an 85:15 mixture that consists of 2-butanone (MEK) and isopropanol. The temperature is lowered to 80° C., and the solution is hot-filtered. The solution is allowed to cool to 5° C., and it is stirred for 7 hours. The crystalline precipitate that is obtained is filtered off, washed with 2-butanone, and then dried in a vacuum at 45-85° C.

A proportion of 500 ppm of 4-MMPPO is detected by analysis using HPLC-MS/MS. The process thus yields a tolperisone end product, which still has additional increasing 4-MMPPO values with extended storage.

Possible variants for the process according to the invention:
Variant I) One or More Recrystallization Cycles:
The tolperisone crude product is dissolved under reflux for 30 minutes in an 85:15 mixture that consists of 2-butanone (MEK) and isopropanol. The temperature is lowered to 80° C., and the solution is hot-filtered. The solution is allowed to cool to 5° C., and it is stirred for 7 hours. The crystalline precipitate that is obtained is filtered off, washed with 2-butanone, and then dried in a vacuum at 45-85° C. The filtering can be done with the addition of an adsorption agent, such as activated carbon or silica gel.

By analysis using HPLC-MS/MS, a proportion of 0.14% by weight of 4-MMPPO is detected that could be reduced to 130 ppm by another recrystallization.

Variant II): Recrystallization and Washing with a 1% HCl-Isopropanol Mixture:
The tolperisone crude product is dissolved under reflux for 12 hours in an 85:15 mixture that consists of 2-butanone (MEK) and isopropanol. The temperature is lowered to 80° C., and the solution is hot-filtered. The solution is allowed to cool to 5° C., and it is stirred for 7 hours at 5° C. The crystalline precipitate is filtered off and washed with 1% HCl-isopropanol mixture, and then dried in a vacuum at 45 to 85° C.

By analysis using HPLC-MS/MS, a proportion of 4-MMPPO in a range of 1.5 to 10 ppm is detected.

Variant III) Recrystallization with a 1% HCl-IPA-MEK Mixture:
The tolperisone crude product is dissolved under reflux for 12 hours in an 85:15 mixture that consists of 2-butanone (MEK) and isopropanol and with the addition of 1% HCl. The temperature is lowered to 80° C., and the solution is hot-filtered. The solution is allowed to cool to 5° C., and it is stirred for 7 hours at 5° C. The crystalline precipitate is filtered off, washed with MEK, and then dried in a vacuum at 45 to 85° C.

By analysis using HPLC-MS/MS, a proportion of 4-MMPPO in a range of 0 ppm (not detectable) to 10 ppm is determined.

Variant IIIa) Recrystallization with a 1% HCl-IPA-MEK+ 5% Citric Acid Mixture:
The tolperisone crude product is dissolved under reflux for 12 hours in an 85:15 mixture that consists of 2-butanone (MEK) and isopropanol and with the addition of 1% HCl and 5% citric acid. The temperature is lowered to 80° C., and the solution is hot-filtered. The solution is allowed to cool to 5° C., and it is stirred for 7 hours at 5° C. The crystalline precipitate is filtered off, washed with MEK, and then dried in a vacuum at 45° to 85° C.

By analysis using HPLC-MS/MS, a proportion of 4-MMPPO in a range of 0 ppm (not detectable) to 10 ppm is determined. This process variant shows the special advantage that citric acid is present in the tolperisone end product and, consequently, a stabilizing effect could be detected.

Variant Iv) Recrystallization with a 1% HCl-IPA-MEK Mixture Plus 5% Citric Acid and Subsequent Washing with an Addition of Acid:
The tolperisone crude product is dissolved under reflux for 12 hours in an 85:15 mixture that consists of 2-butanone (MEK) and isopropanol (IPA) as well as with the addition of 1% HCl and 5% by weight (relative to the active ingredient) of citric acid. The temperature is lowered to 80° C., and the solution is hot-filtered. The solution is allowed to cool to 5° C., and it is stirred for 7 hours at 5° C. The crystalline precipitate is filtered off, washed with MEK, 0.5% HCl and 5% citric acid, and then dried in a vacuum at 45 to 85° C.

By analysis using HPLC-MS/MS, a proportion of 4-MMPPO in a range of 0 ppm (not detectable) to 8 ppm is determined.

Variant V) Recrystallization with a 1% HCl-IPA-MEK Mixture plus 5% Citric Acid and Additional Washing with Highly Volatile Ethereal Solvent:

The tolperisone crude product is dissolved under reflux for 12 hours in an 85:15 mixture that consists of 2-butanone (MEK) and isopropanol (IPA) and with the addition of 1% HCl and 5% by weight of citric acid. The temperature is lowered to 80° C., and the solution is hot-filtered. The solution is allowed to cool to 5° C., and it is stirred for 7 hours at 5° C. The crystalline precipitate is filtered off, washed with MEK, 0.5% HCl and 5% citric acid, washed another time with the same amount of volume of tert-butyl methyl ether, and then dried in a vacuum at 45 to 85° C.

By analysis using HPLC-MS/MS, a proportion of 4-MMPPO in a range of 0 ppm (not detectable) to 10 ppm is determined.

Variant Va) Recrystallization with a 1% HCl-IPA-MEK Mixture plus 5% Citric Acid and Additional Washing with Highly Volatile Ethereal Solvent+5% Citric Acid:

The tolperisone crude product is dissolved under reflux for 12 hours in an 85:15 mixture that consists of 2-butanone (MEK) and isopropanol (IPA) and with the addition of 1% HCl and 5% by weight of citric acid. The temperature is lowered to 80° C., and the solution is hot-filtered. The solution is allowed to cool to 5° C., and it is stirred for 7 hours at 5° C. The crystalline precipitate is filtered off, washed with MEK, 0.5% HCl, washed another time with the same amount of volume of tert-butyl methyl ether, 5% citric acid, and then dried in a vacuum at 50° C.

By analysis using HPLC-MS/MS, a proportion of 4-MMPPO in a range of <1 ppm is determined.

The proportions of piperidine hydrochloride were examined by means of HPLC, whereby values of below 100 ppm to 0 ppm (i.e., not detectable) were determined.

Variant Vb) Industrial Process Example: Recrystallization with a 1% HCl-IPA-MEK Mixture plus 5% Citric Acid and Additional Washing with Highly Volatile, Ethereal Solvent+5% Citric Acid:

165.4 kg of tolperisone crude product is dissolved under reflux for 12 hours in an 85:15 mixture that consists of 2-butanone (MEK, 900 kg) and isopropanol (IPA, 75 kg) with the addition of 1% HCl (6.6 l) and 5% by weight of citric acid (8 kg). The temperature is lowered to 80° C., and the solution is hot-filtered. The solution is allowed to cool to 5° C., and it is stirred for 7 hours at 5° C. The crystalline precipitate is filtered off, washed with MEK (50 l), 0.5% HCl, washed another time with the same amount of volume of tert-butyl methyl ether, 5% citric acid, and then dried in a vacuum at 50° C. Yield 99.9 kg (60.4%).

By analysis using HPLC-MS/MS, a proportion of 4-MMPPO in a range of <1 ppm and a proportion of piperidine hydrochloride of <100 ppm are determined.

The active ingredient tolperisone that is obtained according to the embodiments can be used, according to its analysis, in conventional processes for the production of pharmaceutical formulations, whereby the active ingredient is mixed with the respective pharmaceutical vehicle, granulated and made into tablets, or is taken up in the latter to form a suspension or syrup.

For the production of a film tablet with instant-release properties, the following operating instructions are selected, for example:

EXAMPLE 1

Tableting Via Wet Granulation

A solution that consists of anhydrous citric acid, butanone and isopropyl alcohol is produced. The tolperisone hydrochloride that is produced according to the invention is converted in a granulator, into which the already produced solution is introduced. This mixture is homogenized and then dried in a drier at 60° C. The granulate that is formed is sieved through a 1.8 mm sieve. Silicon dioxide and talcum are added and also mixed. Then, it is mixed with magnesium stearate. Tablets with a diameter of 8 mm and a weight of 155.8-172.2 g are produced. The finished granulate is coated with a suspension that consists of hypromellose/hypromellose phthalate in ethanol/water of dyes and additives in a coating tank at a temperature of 55-60° C. The coated tablets are then dried at room temperature.

EXAMPLE 2

Direct Pressing

A mixture with the following composition is produced:

| Substance | % Proportion |
| --- | --- |
| Tolperisone | 78 |
| Citric Acid, Anhydrous | 3 |
| Primojel | 2.5 |
| Super Tab 22 AN | 16 |
| Aerosil 200 | 0.5 |

The mixture is sieved with a 1.8 mm sieve and pressed directly in a tablet press.

EXAMPLE 3

Dry Granulation

A mixture of the following composition is produced:

| Reagent | % Proportion |
| --- | --- |
| Tolperisone | 72 |
| Citric Acid, Anhydrous | 5 |
| Stearic Acid | 0.5 |
| Super Tab 22 AN | 19.5 |
| Starch 1500 LM | 3 |

The active ingredient and a mixture component are pre-compacted in a dry compacter and then crushed. The granulate is then pressed with a tablet press into tablet cores.

To design a pharmaceutical formulation with controlled release, the procedure can be performed, for example, according to the following formula:

Racemic tolperisone with a proportion of less than 50 ppm of 4-MMPPO is granulated together with a solution that consists of Eudragit RS in 2-butanone. Eudragit S and Eudragit L are then stirred in homogeneously. 5% by weight of citric acid relative to 100% by weight of tolperisone and 4-MMPPO are added to the mixture. The mixture is dried and sieved. The sieved granulation material is mixed with additional additives, such as retardants, and made into tablets, so that the tablet core is obtained. The latter has a diameter of about 8 mm and a weight of 190 mg. The tablet core is then coated with a film that consists of Eudragit L, color pigments, and additional additives, which are dissolved in butanol.

| Content Material | Amount (mg) |
| --- | --- |
| Tolperisone Hydrochloride | 150 |
| Eudragit RS | 1.88 |
| Eudragit L (Core) | 10.50 |
| Eudragit L (Coating) | 3.74 |
| Eudragit S | 10.50 |
| Aerosil | 1.80 |
| Stearic Acid | 1.80 |
| Glycerol Dibehenate | 7.50 |
| Iron Oxide (Pigment) | 0.08 |
| Titanium Dioxide | 4.08 |
| Talcum | 6.03 |
| Polyethylene Glycol | 1.02 |
| Dimethylpolysiloxane | 0.05 |
| Citric Acid | 7.5 |

The use of acid in the tableting process as well as working under anhydrous conditions ensures that the proportion of 4-MMPPO is at least maintained or even additionally reduced.

The transdermal, therapeutic system according to the invention is produced, for example, as an active ingredient patch, whereby the active ingredient tolperisone with a proportion of less than 10 ppm of 4-MMPPO and the components for the adhesive reservoir layer optionally in solution is mixed homogeneously and is applied to the active ingredient-impermeable back side, whereupon optionally the solvent or solvents are removed. Then, the adhesive layer is provided with a corresponding protective layer.

A possible production process can be summarized as follows:

10.0 g of octanoic acid and 10.0 g of isopropyl myristate are mixed while being stirred. Then, 10.0 g of tolperisone hydrochloride with a proportion of less than 50 ppm is incorporated, whereby stirring is continued until the solid is completely dissolved. Then, 130.0 g of a self-cross-linking acrylate copolymer that consists of 2-ethylhexylacrylate, vinyl acetate and acrylic acid, 46% in a solvent mixture (ethyl acetate:heptane:isopropanol:toluene:acetyl acetone=37:26:26:4:1) is added; it is homogenized. Then, an additional 10 g of a methacrylate copolymer based on dimethylamino methacrylate and neutral methacrylic acid esters is sprinkled in while being stirred, and it is stirred for 3 hours at room temperature.

150 g of 52.8% active ingredient-containing adhesive solution, which is painted on an aluminized and siliconized polyethylene film, results. After drying at 60° C., the adhesive film is covered with polyester film. The individual active ingredient patches are punched out with a suitable cutting tool.

The topical formulation according to the invention that contains tolperisone with a proportion of less than 10 ppm of 4-MMPPO can be applied on the skin as a gel, cream or ointment. To increase the bioavailability and simultaneous stabilization of the formulation, carboxylic acids can be used as additives. In this case, it is possible to use the active ingredient in combination with other analgesics.

For the production of a gel, water (145 g) and a sodium hydroxide solution (6 g/5% solution) are mixed. A carbomer (1 g) is slowly stirred into this mixture. Then, 2-propanol (50 g) is stirred in, and the active ingredient in the form of tolperisone hydrochloride (2 g) is stirred in with a proportion of less than 10 ppm of 4-MMPPO.

For the production of a cream, Vaseline (50 g) and cetyl stearyl alcohol (20 g) are melted together until a clear phase is produced. At the same time, a mixture that consists of polysorbate (10 g), glycerol (20 g) and water (98 g) plus citric acid (3 g) and tolperisone hydrochloride with a proportion of less than 50 ppm of 4-MMPPO (2 g) is stirred and added to the molten mass and cold-stirred.

For the production of tolperisone ointment, white Vaseline (92.5 g), cetyl stearyl alcohol (0.5 g), wool wax alcohols (6 g), citric acid (1.5 g) and tolperisone hydrochloride (1 g) are melted together with a proportion of less than 50 ppm of 4-MMPPO and cold-stirred.

In summary, it can be said that by the process according to the invention, for the first time, with respect to the currently applicable guidelines regarding the proportions of substances in pharmaceutical-agent active ingredients that cause side effects, the proportion of 4-MMPPO falls below the maximum permissible value. This is important in as much as the latest guidelines of the FDA and EMEA relative to genotoxic substances (Guideline on the Limits of Genotoxic Impurities CPMP/SWP/5199/02) stipulate a desired content of the same of <1.5 µg/day in pharmaceutical active ingredients and the new pharmaceutical agent approval forbids exceeding the threshold. Since, in the case of 4-MMPPO, genotoxic or carcinogenic actions have been detected in vitro and therefore are also expected in vivo, the requirement exists that only values in the range of below 10 ppm are accepted in a pharmaceutical formulation. Also, these extremely strict criteria can be met for the first time by the process according to the invention as well as by the anhydrous conditions during production of the pharmaceutical formulation in the presence of at least one anhydrous additive, preferably anhydrous citric acid. If an acidic stabilizer is also added to the active ingredient formulation that contains tolperisone that is intended for storage, the undesired secondary reaction can be prevented with formation of 4-MMPPO.

The invention claimed is:

1. A process for the production of tolperisone or one or more pharmaceutically acceptable salts thereof, with less than 10 ppm 4-MMPPO, comprising:

reacting 4-methylpropiophenone,

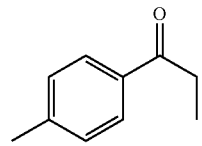

with piperidine hydrochloride

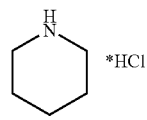

and 1,2-dioxolane

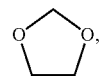

in the presence of one or more acids as a catalyst, filtering off a tolperisone crude product from the reaction mixture in free form or in the form of its pharmaceutically acceptable salts, and recrystallizing the tolperisone crude product in the presence of one or more acids form tolperisone, or one or more pharmaceutically acceptable salts thereof, with less than 10 ppm 4-MMPPO.

2. The process according to claim 1, wherein the reaction of 4-methylpropiophenone, piperidine hydrochloride, and 1,2-dioxolane is performed in the presence of aqueous hydrochloric acid.

3. The process according to claim 1, further comprising reacting 4-methylpropiophenone, piperidine hydrochloride, and 1,2-dioxolane in the presence of one or more solvents.

4. The process according to claim 3, wherein the reaction is performed in 1,2-dioxolane as a solvent.

5. The process according to claim 1, further comprising adding one or more counter-solvents to the reaction of 4-methylpropiophenone, piperidine hydrochloride, and 1,2-dioxolane to precipitate the tolperisone crude product as an addition salt.

6. The process according to claim 1, wherein the recrystallization is carried out from a solvent mixture that comprises one or more of an ether and an alcohol.

7. The process according to claim 1, wherein recrystallizing the tolperisone crude product in the presence of one or more acids comprises adding an acid to the tolperisone or one or more pharmaceutically acceptable salts thereof during the recrystallizing step.

8. The process according to claim 1, wherein the recrystallization is carried out in several stages.

9. The process according to claim 1, further comprising, after the recrystallization, carrying out a drying step.

10. The process according to claim 7, wherein recrystallizing the tolperisone crude product in the presence of one or more acids further comprises adding one or more adsorption agents to the tolperisone.

11. The process according to claim 1, wherein the tolperisone or one or more pharmaceutically acceptable salts thereof with less than 10 ppm 4-MMPPO has less than 7 ppm 4-MMPPO.

12. The process according to claim 11, wherein the tolperisone or one or more pharmaceutically acceptable salts thereof with less than 10 ppm 4-MMPPO has less than 3 ppm 4-MMPPO.

13. The process according to claim 12, wherein the tolperisone or one or more pharmaceutically acceptable salts thereof with less than 10 ppm 4-MMPPO has less than 1.5 ppm 4-MMPPO.

14. The process according to claim 1, further comprising removing piperidine hydrochloride from the tolperisone or one or more pharmaceutically acceptable salts thereof so that the amount of piperidine hydrochloride in the tolperisone or one or more pharmaceutically acceptable salts thereof is less than 100 ppm.

15. The process according to claim 3, wherein the solvent is 1,2-dioxolane.

16. The process according to claim 5, wherein the one or more counter-solvents comprise one or more of ethyl acetate and methyl-tert-butyl ether.

17. The process according to claim 9, wherein the drying step comprises vacuum drying.

18. The process according to claim 10, wherein the one or more adsorption agents comprise one or more of activated carbon and silica gel.

19. A method of recrystallizing crude tolperisone or one or more pharmaceutically acceptable salts thereof comprising
contacting crude tolperisone or one or more pharmaceutically acceptable salts thereof with one or more solvents in the presence of one or more acids; and
forming tolperisone or one or more pharmaceutically acceptable salts thereof with less than 10 ppm 4-MMPPO.

20. The method of claim 19, wherein forming tolperisone or one or more pharmaceutically acceptable salts thereof with less than 10 ppm 4-MMPPO comprises forming tolperisone or a pharmaceutically acceptable salt thereof with less than 7 ppm 4-MMPPO.

21. The method of claim 19 wherein contacting tolperisone or one or more pharmaceutically acceptable salts thereof with one or more solvents comprises dissolving the tolperisone or one or more pharmaceutically acceptable salts thereof in the one or more solvents.

22. The method of claim 21, further comprising heating the one or more solvents.

23. The method of claim 19, wherein the one or more solvents comprise one or more of methyl ethyl ketene and isopropanol.

24. The method of claim 23, wherein the one or more solvents comprise both methyl ethyl ketone and isopropanol.

25. The method of claim 19, wherein the one or more acids comprise hydrochloric acid.

26. The method of claim 19, wherein the tolperisone or one or more pharmaceutically acceptable salts thereof with less than 10 ppm 4-MMPPO has less than 7 ppm 4-MMPPO.

27. The method of claim 26, wherein the tolperisone or one or more pharmaceutically acceptable salts thereof with less than 10 ppm 4-MMPPO has less than 3 ppm 4-MMPPO.

* * * * *

UNITED STATES PATENT AND TRADEMARK OFFICE
CERTIFICATE OF CORRECTION

PATENT NO. : 8,372,979 B2  Page 1 of 1
APPLICATION NO. : 12/597722
DATED : February 12, 2013
INVENTOR(S) : Welzig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 477 days.

Signed and Sealed this
First Day of September, 2015

Michelle K. Lee
*Director of the United States Patent and Trademark Office*